United States Patent
Elwood et al.

(10) Patent No.: US 6,805,172 B2
(45) Date of Patent: Oct. 19, 2004

(54) ENHANCED/PROACTIVE $CO_2/O_2$ GAS CONTROL

(75) Inventors: Bryan M. Elwood, Candler, NC (US); Richard H. Bair, III, Weaverville, NC (US)

(73) Assignee: Kendro Laboratory Products, Inc., Asheville, NC (US)

( * ) Notice: Subject to any disclaimer, the term of this patent is extended or adjusted under 35 U.S.C. 154(b) by 0 days.

(21) Appl. No.: 10/235,796

(22) Filed: Sep. 6, 2002

(65) Prior Publication Data

US 2004/0045624 A1 Mar. 11, 2004

(51) Int. Cl.⁷ .............................................. B65B 31/00
(52) U.S. Cl. .............................. 141/49; 141/4; 141/39; 141/54; 141/83; 141/94
(58) Field of Search .............................. 141/4, 7, 9, 18, 141/37, 39–40, 44, 47, 49–51, 52, 54, 83, 94, 95, 100, 104, 192, 197

(56) References Cited

U.S. PATENT DOCUMENTS

| | | | | |
|---|---|---|---|---|
| 4,527,600 A | * | 7/1985 | Fisher et al. | 141/4 |
| 5,628,349 A | * | 5/1997 | Diggins et al. | 141/3 |
| 5,868,176 A | * | 2/1999 | Barajas et al. | 141/83 |
| 5,881,779 A | * | 3/1999 | Kountz et al. | 141/83 |

* cited by examiner

*Primary Examiner*—Timothy L. Maust
(74) *Attorney, Agent, or Firm*—Baker & Hostetler LLP

(57) ABSTRACT

An apparatus and method for compensating gas loss in an incubator. A transducer can be used to monitor the gas pressure of various gases that flow into the incubator. By knowing the correct pressure that flows into the chamber, a faster and more accurate compensation can be done during enhancement or depletion of the gases in the incubator.

17 Claims, 2 Drawing Sheets

ENHANCED/PROACTIVE $CO_2/O_2$ GAS CONTROL

FIELD OF THE INVENTION

Embodiments of the present invention generally relate to an apparatus and method for use with a controlled gas atmosphere. More particularly, the apparatus and method of the present invention relates to enhancing $CO_2$, $N_2$, and $O_2$ gas control in an incubator.

BACKGROUND OF THE INVENTION

There are a number of commercial applications that utilize a controlled gas atmosphere enclosure. For example, in the semiconductor industry, gases are injected into an enclosed chamber wherein one of the gases is plasmarized and strikes a target on a chamber lid causing the target's materials to deposit on a wafer. Other commercial applications include using controlled gases to cultivate biological cultures in an enclosed chamber, such as an incubator.

A conventional incubator is generally rectangular in shape and has up to five insulated walls (top, bottom, left side, right side, and rear). Each wall may have an inner space defined by the inner and outer surfaces of the insulated wall and the inner spaces can be in communication with each other. An insulated front door together with the insulated walls complete the inner chamber of the incubator and the door is typically mounted on hinges on the front side of one of the side walls. The door allows access into the inner chamber where culture plates are placed or removed from the shelves that are provided therein.

It is desirable to maintain optimal conditions inside the incubator in order to promote the desired growth of the cultures and to document the experiment for repeatability by others. In a conventional incubator, gases such as $O_2$, $N_2$, and $CO_2$ are introduced from their respective supply tanks into the chamber depending on the growing conditions desired by the user. Typically, the user sets the $CO_2$ and $O_2$ setpoints and the appropriate gases are added. $N_2$ can be used to purge excess $O_2$ from the incubator when the $O_2$ level in the chamber is too high for the setpoints.

During the operation of the incubator, the gases contained therein can escape by leaking out through gaps in the seals of the door or when the door is opened and closed. Fluctuations in the gas contents of the incubator can damage the samples or alter the experiment data. Thus, it is important to prevent fluctuations of the gas content by monitoring and compensating for the gases that are lost in order to decrease recovery time. The faster the recovery time, the less time the samples are subjected to differing atmospheres. Conventional incubators can provide feed back of the gases that are lost through a compensation system. However, the compensation system is prone to sensor and system latencies. For example, delays in reporting by a sensor can cause the compensation system to overcompensate and inject more gas than necessary, leading to more fluctuations in the incubator and a longer recovery time. Additionally, delays in reporting time by the sensor can cause the compensation system to under compensate leading to possible destruction of the samples due to longer recovery time.

Other conventional compensation systems can make injection decisions based on an ideal physics model of the incubator. By using the ideal physics model, the system and sensor latencies can be removed, however, this system assumes that the user followed the instructions for proper pressure settings, that the gas instrumentation is accurate, and that the gas supply is under a constant pressure. These factors, if not working properly, can cause additional delays in the compensation system of the incubator.

Therefore, there is a need to further enhance rapid gas concentration recovery systems by providing a pressure input for the gas or gases involved rather than assuming a known pressure based on a manual setting of the gas or gases by the user.

SUMMARY OF THE INVENTION

The present invention generally relates to a compensation system to allow a faster recovery during enhancement or depletion of an incubation chamber of an incubator. The faster recovery rate will help to ensure optimal conditions in the chamber for optimal growth of the cultures.

In one embodiment of the present invention, a gas compensation apparatus for an enclosed chamber is provided and can include a gas monitor that can monitor the pressure of a gas being injected into the chamber, a gas injection determiner that can determine the amount of the gas that is required during compensation, and at least one gas supply source for supplying at least one gas into the chamber, wherein the gas monitor, the gas injection determiner and the at least one gas supply source can be in communication with each other. The gas monitor can be a transducer and the compensation can be enhancement of the chamber with the at least one gas. The gas compensation can also be depletion with the at least one gas in the chamber. The gas injection determiner can determine the amount of gas via a formula, wherein the formula can be selected from $X(t)=V+(X(0)-V)*e^{-(q*t/V)}$ and $X(t)=(q*V/(q+q_1))+(X(0)-(q*V/(q+q_1)))*e^{(-(q+q_1)*t/V)}$. The gas injection determiner can determine the amount of gas via a formula, wherein the formula can be selected from $X(t)=X(0)*e^{-(q*t/V)}$ and $X(t)=X(0)*e^{(-(q+q_1)*t/V)}$. Additionally, the definition of q and $q_1$ can be selected from $[2.90+[(P-10)*0.79]/5]/60$ standard liters/sec, when $10 \leq P \leq 15$ psig and $[3.69=[(P-15)*2]/15]/60$ standard liters/sec, when $15 \leq P \leq 30$ psig. The definition of q and $q_1$ can be selected from $[2.90+[(P-10)*0.79]/5]/60$ standard liters/sec, when $10 \leq P \leq 15$ psig and $[3.69=[(P-15)*2]/15]/60$ standard liters/sec, when $15 \leq P \leq 30$ psig. The q and $q_1$ can be multiplied by a correction value and the correction value can be selected from $CO_2=0.808$, for $O_2=0.95$, and for $N_2=1.01$. The q and $q_1$ can be multiplied by a correction value and the correction value can be selected from $CO_2=0.808$, for $O_2=0.95$, and for $N_2=1.01$.

In another embodiment of the invention, a method of compensation is provided and can include determining what compensation is need in the chamber, determining the pressure of at least one gas that is injected into the chamber, and injecting the at least one gas into the chamber during compensation. The compensation may be enhancement by injecting at least one gas into the chamber and may be depletion by injecting at least one gas into the chamber. Determining the pressure may be done via a transducer. Injecting the at least one gas can include injection based on a formula selected from $X(t)=V+(X(0)-V)*e^{-(q*t/V)}$, $X(t)=(q*V/(q+q_1))+(X(0)-(q*V/(q+q_1)))*e^{(-(q+q_1)*t/V)}$, $X(t)=X(0)*e^{-(q*t/V)}$ and $X(t)=X(0)*e^{(-(q+q_1)*t/V)}$. The definition of q and $q_1$ can be selected from $[2.90+[(P-10)*0.79]/5]/60$ standard liters/sec, when $10 \leq P \leq 15$ psig and $[3.69=[(P-15)*2]/15]/60$ standard liters/sec, when $15 \leq P \leq 30$ psig. The q and $q_1$ can be multiplied by a correction value, the correction value can be selected from $CO_2=0.808$, for $O_2=0.95$, and for $N_2=1.01$.

In still another embodiment a compensation system for an enclosed chamber can include means for determining if compensation is needed in the chamber, means for monitoring a pressure of a gas in the chamber, means for determining the amount of at least one gas to inject into the chamber during compensation, and means for injecting the at least one gas, wherein the means for determining, the means for monitoring, the means for determining and the means for injecting can be in communication with each other. The means for determining if compensation is needed can be a controller means. The means for monitoring the pressure can be a transducer means. The means for determining amount of least one gas can be based on a formula selected from $X(t)=V+(X(0)-V)*e^{-(q*t/V)}$, $X(t)=(q*V/(q+q_1))+(X(0)-(q*V/(q+q_1)))*e^{(-(q+q_1)*t/V)}$, $X(t)=X(0)*e^{-(q*t/V)}$ and $X(t)=X(0)*e^{(-(q+q_1)*t/V)}$. The definition of q and $q_1$ can be selected from $[2.90+[(P-10)* 0.79]/5]/60$ standard liters/sec, when $10 \leq P \leq 15$ psig and $[3.69=[(P-15)*2]/15]/60$ standard liters/sec, when $15 \leq P \leq 30$ psig. The q and $q_1$ can be multiplied by a correction value, the correction value can be selected from $CO_2=0.808$, for $O_2=0.95$, and for $N_2=1.01$. The means for injecting the at least one gas can be done by injecting gas from a gas supply tank at a predetermined flow rate and pressure.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

The present invention provides a method and apparatus to enhance $CO_2$, $N_2$, and $O_2$ injections during compensation. A transducer, as described herein, can be located anywhere (between the hose and the inlet or embedded in the inlet), as long as it can monitor the volume, pressure or flow rate of the gas being injected at the gas inlet. The transducer can be the MPX5050GP™ from Motorola (Austin, Tex.). The inlet can be an orifice, such as a Sapphire Orifice #48, from O'Keefe Controls Co. (Trumbull, Conn.). However, one skilled in the art will recognize the embodiments of the invention herein can be adapted, including the equations herein, so that other inlets and orifices can be utilized with the incubator.

Figure 1:
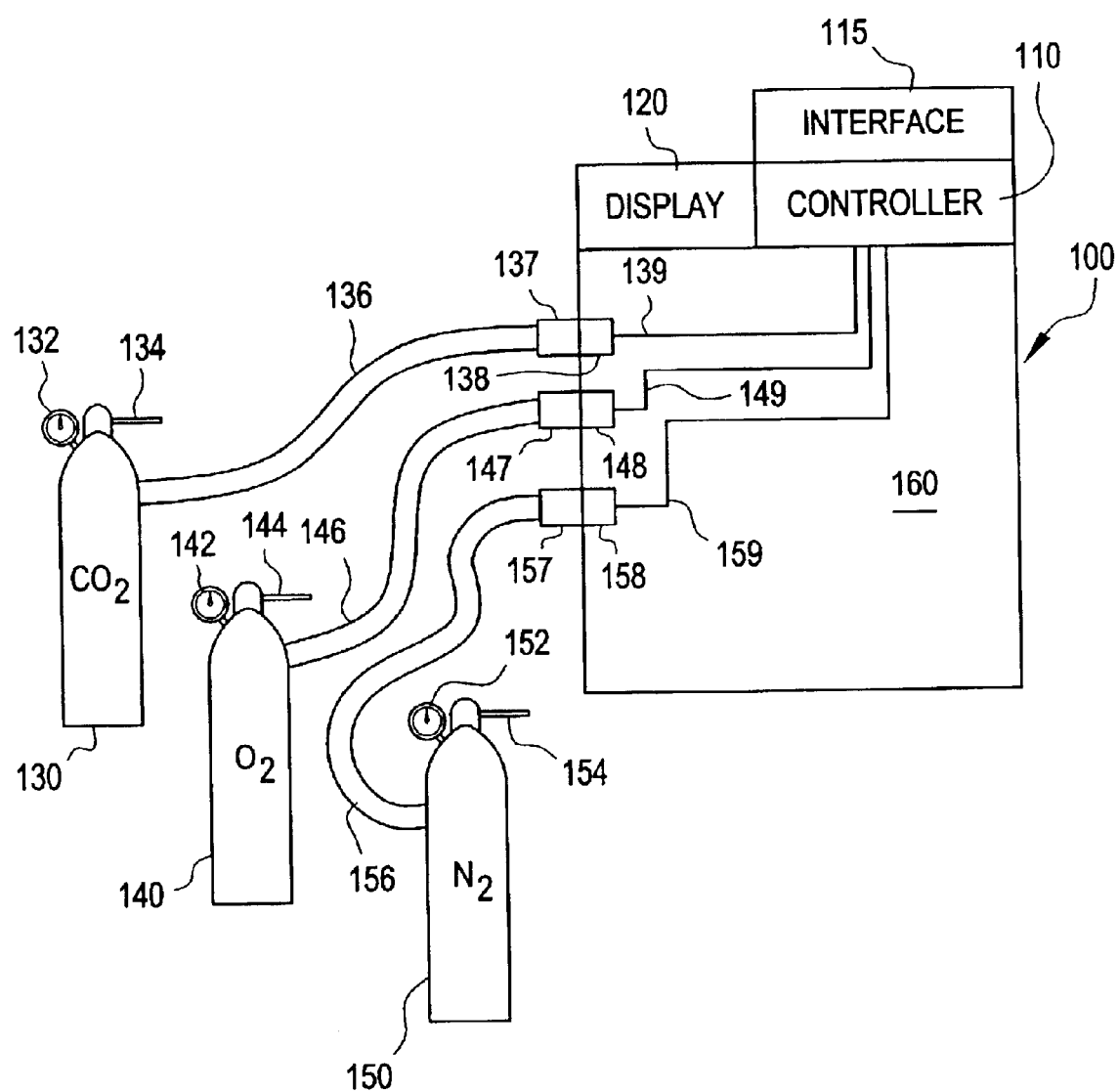
FIG. 1 is one embodiment of an apparatus of the present invention.

FIG. 1 is one embodiment of an apparatus of the present invention. An incubator 100 having a chamber 160, a controller 110, an interface 115, and a display 120. The incubator 100 is connected to various gas supply tanks, such as a $CO_2$ tank 130, an $O_2$ tank 140 and a $N_2$ tank 150. The gas supply tanks 130, 140, and 150 contain $CO_2$, $O_2$, and $N_2$, respectively and these gases are typically used in a tri-gas incubator. However, one skilled in the art will recognize that any gas can be used with the present invention. The controller 110 is embedded in the incubator 100 or can be remotely located, such as in a computer. The controller 110 can include a central processing unit (CPU), a memory, and support circuits. The controller 110 controls, executes algorithms, and monitors various aspects and operations of the incubator 100. Additionally, the controller 110 monitors the pressure, the flow rate, and the volume of the gas that flows through inlets 137, 147 and 157 via transducers 138, 148, and 158. The inlets 137, 147, and 157 are each an orifice, such as a Sapphire Orifice #48, and the transducers 138, 148, and 158 are each a MPX5050GP™ transducer from Motorola. However, other orifices of varying sizes and shapes or transducers can be used.

The controller 110 monitors as many inlets 137, 147 and 157 as the user desires via the transducers 138, 148, and 158. The transducer 138, 148, and 158 communicate with the controller 110 via relay lines 139, 149, and 159. The transducers 138, 148, 158 can have a self-contained power source or may receive power from the relay lines 139, 149 and 159 or other sources.

The controller 110 is in communication with the display 120, which displays data or information about the status and operating parameters of the incubator 100. The interface 115 allows the user to interact with the incubator 100 and controller 110 via a preprogrammed menu. The user also uses the interface 115 to set the setpoint for each gas that will be injected into the chamber 160.

The $CO_2$ gas supply tank 130 includes a first pressure dial 132, a first handle 134, and a first gas hose 136. The first pressure dial 132 displays the current pressure of the $CO_2$ gas that is suppose to flow into the first gas hose 136. The current pressure can be set by adjusting the first handle 134, in a first direction (to increase the pressure) or in a second direction (to decrease the pressure). The $CO_2$ gas travels in the first gas hose 136 to the first gas inlet 137, where the $CO_2$ gas flows into the chamber 160. The transducer 138 provides information about the pressure at the gas inlet 137 and the controller 110 can calculate the gas flow rate based on the gas type and orifice characteristics.

The $O_2$ gas supply tank 140 includes a second pressure dial 142, a second handle 144, and a second gas hose 146. The second pressure dial 142 displays the current pressure of the $O_2$ gas that is suppose to flow into the second gas hose 146. The current pressure for the $O_2$ gas is set by the user turning the second handle 144 in the first or second direction to allow the $O_2$ gas to flow into the second gas hose 146. The second gas hose 146 is attached to the second gas inlet 147, where the $O_2$ gas can flow into the chamber 160. The transducer 148 provides information about the pressure at the gas inlet 147 and the controller 110 can calculate the gas flow rate based on gas type and orifice characteristics.

The $N_2$ gas supply tank 150 includes a third pressure dial 152, a third handle 154, and third gas hose 156. The third pressure dial 152 displays the current pressure of the $N_2$ gas that is suppose to flow into the third gas hose 156. The current pressure of the $N_2$ gas can be set by the user by turning the third handle 154 in a first or second direction to allow the $N_2$ gas to flow into the third gas hose 156. The third gas hose 156 can be attached to the third gas inlet 157, where the $N_2$ gas can flow into the chamber 160. The transducer 158 provides information about the pressure at the gas inlet 157 and the controller 110 can calculate the gas flow rate based on gas type and orifice characteristics.

Samples are typically placed in the incubator 100 in order to grow in a controlled atmosphere. The samples can be placed on shelves of the chamber 160 and gases are introduced at certain pressures from gas supply tanks 130, 140, and 150 into the chamber in order to control the atmosphere of the chamber. If the incubator's door remains closed, then any gas that leaks out through the incubator seals is typically negligible. Therefore, conventional steady-state algorithms are typically employed when concentrations are at or near a setpoint of the gas. Rapid recovery mechanisms are used when large deviations from actual gas concentration(s) to setpoint concentration(s) exist, such as those present after a door opening event. In addition, other samples from other experiments can also share the chamber 160, and thus, the incubator's door is opened and closed many times throughout the day leading to large gas fluctuations. Thus, ideally the incubator should recover quickly in order to prevent large fluctuations of gas concentrations and harm to the samples.

The user sets the setpoints or concentration of gas for $CO_2$ and $O_2$ that the incubator 100 will be operating at. The controller 110 monitors the amount and pressure of each gas being injected, via the respective transducers, 138, 148 and 158. When the door is opened and closed throughout the day, various gases will escape into the atmosphere and have to be replaced or compensated. The sensors will relay the remaining concentration of the various gases in the chamber 160 so that depending on the setpoints, the controller 110 can compensate for the various gas loss through enhancement or depletion.

During enhancement, gases, such as $CO_2$, can be injected into the chamber 160 to bring the $CO_2$ to the setpoint level. In order for the controller 110 to calculate the proper injection amount of $CO_2$ during enhancement, formula (I) can be used to determine the volume of the chamber 160 at a given time. During depletion, when the $O_2$ levels are too high for the setpoint of $O_2$, then $N_2$ can be injected in order to displace the $O_2$ concentration in the chamber 160. In order for the controller 110 to calculate the proper injection amount of $N_2$ during depletion, formula (II) can be used to determine the volume of the chamber 160 at a given time.

$$\text{Enhancement: } X(t)=V+(X(0)-V)*e^{-(q*t/V)} \quad (I)$$

$$\text{Depletion: } X(t)=X(0)*e^{-(q*t/V)} \quad (II)$$

Where:
$X(t)$=volume of gas X (in liters) at time t
V=Total volume of the incubator
$X(0)$=volume of gas at t=0 (current volume before injection)
q=gas flow (liters/sec)
t=time (seconds)

These equations (I & II) compensate for a single gas injection (though could be used in multiple gas systems). Moreover, as the chamber 160 is not pressurized, injection of one gas affects the concentration of the other. Therefore, as incubators typically control up to two gas concentrations ($CO_2$ and $O_2$), in practice, equations I and II are useful for single gas (typically $CO_2$) control only.

For a TriGAS incubator, where $CO_2$, $O_2$ and $N_2$ gases are used the equation are:

$$\text{Enhancement: } X(t)=(q*V/(q+q_1))+(X(0)-(q*V/(q+q_1)))*e^{-(q+q_1)(t/V)} \quad (III)$$

$$\text{Depletion: } X(t)=X(0)*e^{-(q+q_1)*t/V} \quad (IV)$$

Where:
$X(t)$=volume of gas X (in liters) at time t
V=Total volume of the incubator
$X(0)$=volume of gas at t=0 (current volume before injection)
q=gas flow (liters/sec)
t=time (seconds)
$q_1$=second gas flow (liters/sec)

A person skilled in the art will notice that if $q_1$ is 0, then both equations (III & IV) reduce mathematically to equations I & II, respectively. Depending on the criteria of the product, one gas may inject serially first for the fastest recovery of that gas' concentration. However, this is at the expense of the second gas' recovery, as it is delayed. In the preferred embodiment, both gases inject simultaneously.

In this case, most likely both gases will not achieve its respective setpoint at the same time. Therefore, in practice, equations III & IV are solved for time (t) using:

$$t=(-V/(q+q_1))*ln((X(t)*(q+q_1)-q*V)/(X(0)*(q+q_1)-q*V)) \quad (V)$$

$$t=(-V/(q+q_1))*ln(X(t)/X(0)) \quad (VI)$$

where the other variables are the same as above, except that $X(t)$ is based on the user entered setpoint concentration and tank volume and $X(0)$ is based on the start conditions of the recovery system; i.e., current gas concentration. The times for both gases assume that both gases are injecting up to the time when one gas achieves its setpoint; that is, this equation will be solved for both gas injections and the smaller time will be the point at which the first gas no longer is injected. At this point, the volume of the gas that has yet to reach its setpoint is remembered and the additional time for that gas to recover is solved for using $q_1$=0, as the first gas has already achieved its setpoint. Of course, during this time of injection, only the second gas is injected, but the first gas will be affected. Therefore in practice, typically the loss is calculated, and the first gas to achieve the setpoint is injected at an averaged rate over the remaining time that the second gas is injected. At this time, additional loss iterations can be performed and then both gases enter steady state maintenance.

In some embodiments, $O_2$ control is mutually exclusive that is, the $N^2$ or $O_2$ gas supply tank is connected not both. Therefore, "look-ahead" calculations may be necessary in the depletion mode only. For example, if $O_2$ (depleted via $N_2$) has the lesser time calculations, then $CO_2$ will continue to inject and over deplete $O_2$ as there is only a $CO_2$ and $N_2$ source in depletion mode, this situation must be avoided.

Of the above variables, q and $q_1$ can be unreliable because of the gas flow and pressure at the inlets 137, 147, and 157 are dependent on various factors and thus, can fluctuate leading to longer compensation time. The gas pressure can be set by the user, however, errors can occur if the pressure is not monitored. For example, the pressure is set by the user via the handles 134, 144, and 154, however, if the user is not attentive, he can set the pressure at the wrong setting. Another problem is that the gauges 132, 142, and 152 can malfunction and thus, the gauge needle can display the incorrect pressure, leading the user to believe that the correct pressure was set. Other errors can occur if the gas hoses 136, 146, and 156, and/or the gas inlets 137, 147, and 157 are obstructed causing the pressure to fluctuate from the desired settings. By having the transducers 138, 148, and 158 monitor the gas pressure and gas flow of the gas that actually enters the chamber 160, a more accurate compensation (depletion or enhancement) by the controller 110 is accomplished leading to better compensation time.

Once the respective transducers 138, 148, and 158 establish the proper pressure for the respective gas inlets 137, 147 and 157, the variables q and $q_1$ can be solved by the controller using the following equations:

For $10 \leq P \leq 15$ psig;

$$\text{then } q=[2.90+[(P-10)*0.79]/5]/60 \text{ standard liters/sec} \quad \text{(VII)}$$

Where:
q=gas flow (liters/sec)
2.90=air flow through the Sapphire orifice #48 at 10 psig
$[(P-10)*0.79]/5$=linearizes correction factor for flow between 11 & 14 psig.
60=converts expression from minutes to liters/sec For $15 \leq P \leq 30$ psig;

$$\text{then } q=[3.69=[(P-15)*2]/15]/60 \text{ standard liters/sec} \quad \text{(VIII)}$$

Where
q=gas flow (liters/sec)
3.69=air flow through the Sapphire orifice #48 at 15 psig
$[(P-15)*2]/15$=linearizes correction factor for flow between 16 & 30 psig.
60=converts expression from minutes to liters/sec These expressions hold true for airflow thus, the expression needs to be further refined for the particular gas injected. For example, if 1 liter/min of air flows through the inlet at a particular pressure, then at the same pressure, 0.808 liter/min of $CO_2$ will flow through it. Thus, correction factors for the specific gas are multiplied to q to get the corrected q value. The correction values for the various gases are:

For $CO_2$=0.808
For $O_2$=0.95
For $N_2$=1.01

Once q and/or $q_1$ are corrected with the proper correction value, it can be plugged back into the equations.

Figure 2:
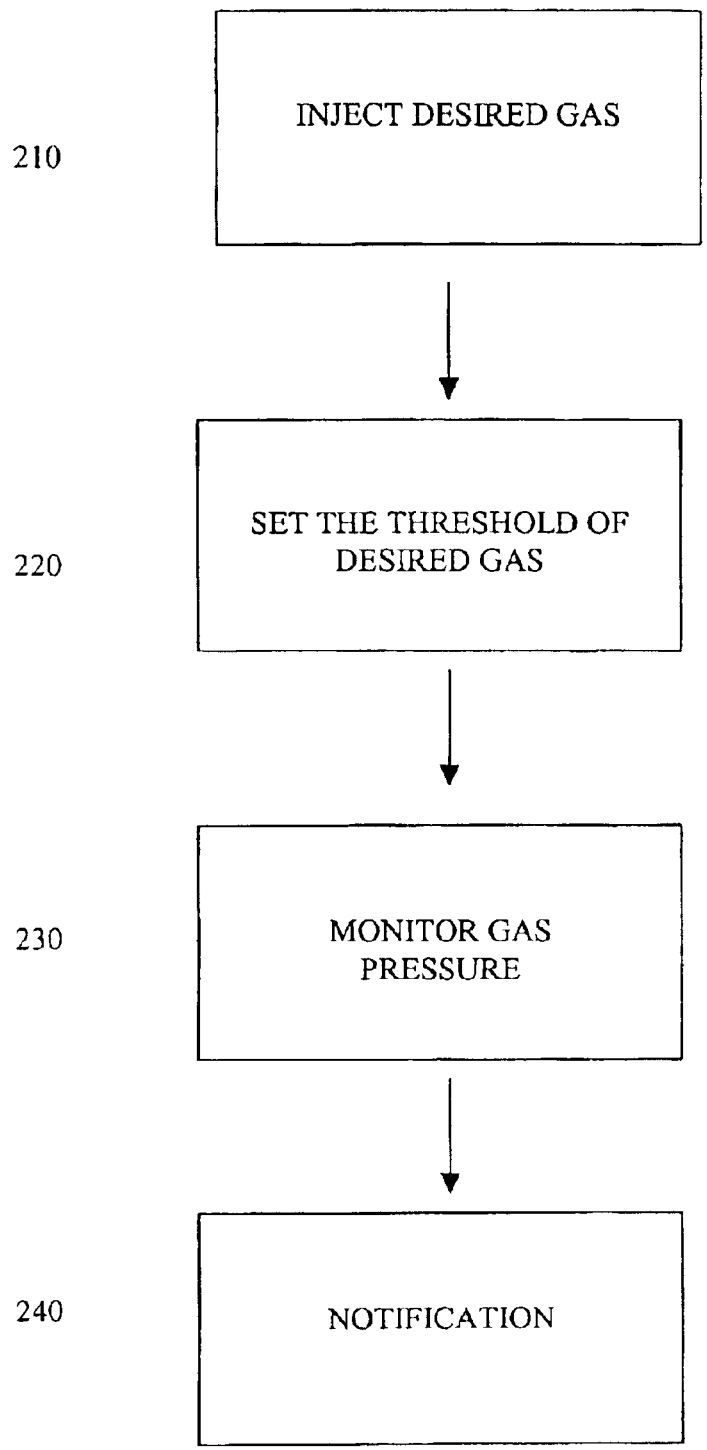
FIG. 2 is a flowchart of an embodiment of the present invention.

FIG. 2 is a flowchart 200 of an embodiment of the present invention. The flow chart 200 starts at step 210, where a determination of whether enhancement, depletion or no action is required based on previous setpoints for gases, such as $CO_2$, $O_2$, or any other desired gas, and the conditions that are monitored by sensors in the chamber 160. If no action is needed (step 220), then wait until the next determination period starts (step 230) and return (step 235) to step 210. The next determination period (step 210) can be a set time or any time the user requires due to the conditions in the chamber 160. At step 240, the pressure is measured by the transducers 138, 148, and 158 at the respective gas inlets 137, 147 and 157 and relayed to the controller 110 for calculation. At step 250, using the appropriate equation III or IV based on the pressure determined by the transducers 138, 148, and 158, the controller 110 can determine the value of q. Then, the appropriate correction factor (depending on what gas) is multiplied by q to provide the corrected value of q. At step 260, the corrected value of q is inserted into equation I or II depending on whether the chamber 160 needs to be enhanced or depleted, so that a more accurate enhancement or depletion of the chamber can be accomplished by the controller 110.

Because the compensation system provided herein allows for a faster recovery time of the gas or gases lost during the operation of the incubator 100, the samples can be cultivated in a more stable atmosphere. With the transducers 138, 148 and 158 providing accurate pressure readings to the controller 110, the controller can better compensate for the gas lost. The transducers 138, 148 and 158 used with the compensation system help to correct human errors that may be made during setting of the pressure, to detect any clogs in the hose lines or the inlets, or detect errors in the pressure gauge at the supply tanks, so that a more accurate and faster compensation of gas loss is provided to the chamber 160. Because the compensation system is more efficient, the user can save money and run better experiments with the samples.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A gas compensation apparatus for an enclosed chamber, comprising:
    a gas monitor that monitors the pressure of a gas being injected into the chamber;
    a gas injection determiner that determines the amount of the gas that is required during compensation; and
    at least one gas supply source for supplying at least one gas into the chamber, wherein the gas monitor, the gas injection determiner and the at least one gas supply source are in communication with each other and the at least one gas is selected from the group consisting of $CO_2$, $N_2$ and $O_2$,
    wherein the chamber is not pressurized.

2. The gas compensation apparatus of claim 1, wherein the gas monitor is a transducer.

3. The gas compensation apparatus of claim 1, wherein compensation is enhancement of the chamber with the at least one gas.

4. The gas compensation apparatus of claim 1, wherein compensation is depletion with the at least one gas in the chamber.

5. The gas compensation apparatus of claim 1, wherein the gas injection determiner determines an enhancement amount of gas injection via a formula, wherein the formula is selected from a group consisting of $X(t)=V+(X(0)-V)*e^{-(q*t/v)}$ for a single gas injection and $X(t)=(q*V(q+q_1))+(X(0)-(q*V/(q+q_1)))*e^{(-(q+q_1)*t/V)}$ for a multi-gas injection, where X(t) is the volume of gas X (in liters) at time t, V is the total volume of the chamber. X(0) is the volume of gas at t=0 (current volume before injection), q is gas flow (liters/sec), and $q_1$ is the second gas flow (liters/sec).

6. The gas compensation apparatus of claim 1, wherein the gas injection determiner determines a depletion amount of gas via a formula, wherein the formula can be selected from a group consisting of $X(t)=X(0)*e^{-(q*t/V)}$ for a single gas depletion and $X(t)=X(0)*e^{(-(q+q_1)*t/V)}$ for a multi-gas depletion, where X(t) is the volume of gas X (in liters) at time t, V is the total volume of the chamber, X(0) is the volume of gas at t=0 (current volume before injection), q is gas flow (liters/sec), and $q_1$ is the second gas flow (liters/sec).

7. The gas compensation apparatus of claim 5, wherein the definition of q and $q_1$ can be selected from a group consisting of [2.90+[(P−10)*0.79]/5]/60 standard liters/sec, when 10≦P<15 psig and [3.69=[(P−15)*2]/15]/60 standard liters/sec, when 15≦P≦30 psig.

8. The gas compensation apparatus of claim 6, wherein the definition of q and $q_1$ can be selected from a group consisting of [2.90+[(P−10)*0.79]/5]/60 standard liters/sec, when 10≦P<15 psig and [3.69=[(P−15)*2]/15]/60 standard liters/sec, when 15≦P≦P≦30 psig.

9. The compensation apparatus of claim 7, wherein q and $q_1$ are multiplied by a correction value and the correction value can be selected from a group consisting of for $CO_2$= 0.808, for $O_2$=0.95, and for $N_2$=1.01.

10. The compensation apparatus of claim 8, wherein q and $q_1$ are multiplied by a correction value and the correction value can be selected from a group consisting of for $CO_2$= 0.808, for $O_2$=0.95, and for $N_2$=1.01.

11. A compensation system for an enclosed chamber comprising:

means for determining if compensation is needed in the chamber;

means for monitoring a pressure of a gas in the chamber;

means for determining the amount of at least one gas to inject into the chamber during compensation; and means for injecting the at least one gas, wherein the means for determining, the means for monitoring, the means for determining and the means for injecting are in communication with each other, wherein and the at least one gas is selected from the group consisting of $CO_2$, $N_2$ and $O_2$ and wherein the chamber is not pressurized.

12. The compensation system of claim 11, wherein the means for determining if compensation is needed is a controller means.

13. The compensation system of claim 11, wherein the means for monitoring the pressure is a transducer means.

14. The compensation system of claim 11, wherein the means for determining amount of least one gas is based on a formula selected from a group consisting of $X(t)=V+(X(0)-V)*e^{-q*t/V}$ for a single gas injection, and $X(t)=(q*V/(q+q_1))+(X(0)-(q*V/(q+q_1)))*e^{(-(q+q_1)*t/V)}$ for a multi-gas injection, $X(t)=X(0)*e^{-(q*t/V)}$ for a single gas depletion and $X(t)=X(0)*e^{(-(q+q_1)*t/V)}$ for a multi-gas depletion, wherein X(t) is the volume of gas X (in liters) at time t, V is the total volume of the chamber, X(0) is the volume of gas at t=0 (current volume before injection), q is gas flow (liters/sec), and $q_1$, is the second gas flow (liters/sec).

15. The compensation system of claim 14, wherein the definition of q and $q_1$ can be selected from a group consisting of [2.90+[(P−10)*0.79]/5]/60 standard liters/sec, when 10≦P<15 psig and [3.69=[(P−15)*2]/15]/60 standard liters/sec, when 15≦P≦30 psig.

16. The compensation system of claim 15, wherein q and $q_1$ are multiplied by a correction value, the correction value can be selected from a group consisting of for $CO_2$=0.808, for $O_2$=0.95, and for $N_2$1.01.

17. The compensation system of claim 11, wherein the means for injecting the at least one gas is done by injecting gas from a gas supply tank at a predetermined flow rate and pressure.

* * * * *